US00PP31962P3

(12) United States Plant Patent
van Geest

(10) Patent No.: US PP31,962 P3
(45) Date of Patent: Jul. 14, 2020

(54) ***FICUS* PLANT NAMED 'ESFIBE1801'**

(50) Latin Name: *Ficus benjamina*
Varietal Denomination: ESFIBE1801

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,275

(22) Filed: Mar. 16, 2019

(65) Prior Publication Data

US 2020/0113096 P1 Apr. 9, 2020

(30) Foreign Application Priority Data

Oct. 9, 2018 (QZ) ..... PBR 20182550

(51) Int. Cl.
*A01H 5/00* (2018.01)
*A01H 6/00* (2018.01)
*A01H 5/08* (2018.01)

(52) U.S. Cl.
USPC ..... Plt./211
CPC ..... *A01H 6/00* (2018.05); *A01H 5/08* (2013.01)

(58) Field of Classification Search
USPC ..... Plt./211
CPC ... A01H 5/00; A01H 5/08; A01H 5/12; A01H 6/00
See application file for complete search history.

*Primary Examiner* — June Hwu
(74) *Attorney, Agent, or Firm* — Samuel R. McCoy, Jr.

(57) ABSTRACT

A new and distinct variety of *Ficus* plant named 'ESFIBE1801' which is characterized by the combination of relatively small foliage, foliage with undulating margins and an elongated aristate to caudate apex, foliage with a relaxed attitude, light green young foliage and dark green mature foliage, and the stability of all characteristics from generation to generation.

2 Drawing Sheets

CROSS REFERENCE TO RELATED APPLICATIONS

This application claims priority to the Community Plant Variety Rights application number 2018/2550, filed Oct. 9, 2018, which is herein incorporated by reference.

Latin name of the genus and species: The Latin name of the genus and species of the novel variety disclosed herein is *Ficus benjamina*.

Variety denomination: The inventive variety of *Ficus* disclosed herein has been given the variety denomination 'ESFIBE1801'.

BACKGROUND OF THE INVENTION

Parentage: 'ESFIBE1801' originated as a naturally occurring, whole-plant mutation of *Ficus benjamina* 'Danielle' (Community Plant Variety Rights grant number 590). In the summer of 2016, the inventor discovered the mutation at his commercial greenhouse in Gravenzande, The Netherlands, growing amongst a cultivated population of 'Danielle' plants. The mutation was noted for its upright habit and dark green foliage with an undulating margin and elongated apex and was subsequently isolated for further evaluation in order to confirm the distinctness and stability of the characteristics first observed. Upon confirmation of distinctness and stability, 'ESFIBE1801' was selected for commercialization.

Asexual Reproduction: Asexual reproduction of ESFIBE1801', by way of stem cuttings, was first initiated in the summer of 2016 at a commercial greenhouse in Gravenzande, The Netherlands. Through five subsequent generations, the unique features of this cultivar have proven to be stable and true to type.

SUMMARY OF THE INVENTION

The cultivar 'ESFIBE1801' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESFIBE1801'. These characteristics in combination distinguish 'ESFIBE1801' as a new and distinct *Ficus* cultivar:

1. *Ficus* 'ESFIBE1801' exhibits relatively small foliage with undulating margins and an elongated aristate to caudate apex; and
2. *Ficus* 'ESFIBE1801' exhibits foliage with a relaxed attitude; and
3. *Ficus* 'ESFIBE1801' exhibits light green young foliage and dark green mature foliage.

BOTANICAL DESCRIPTION OF THE PLANT

Figure 1:
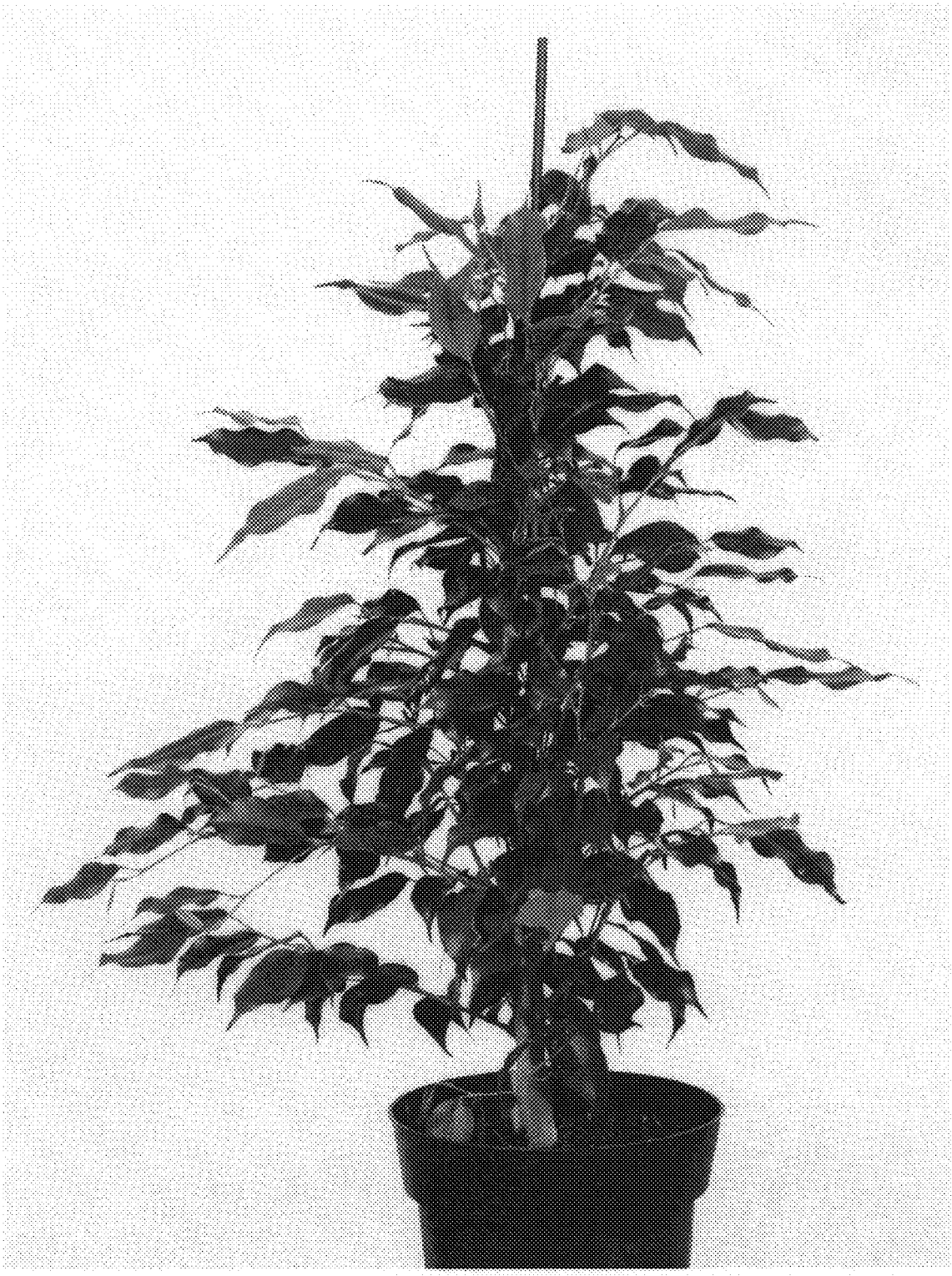
FIG. 1 illustrates, as nearly true as it is reasonably possible to make the same in color photographs of this type, an exemplary plant of 'ESFIBE1801' grown in a commercial greenhouse in Gravenzande, The Netherlands. This plant is approximately 26 weeks old, shown planted in a 15 cm container.
Figure 2:
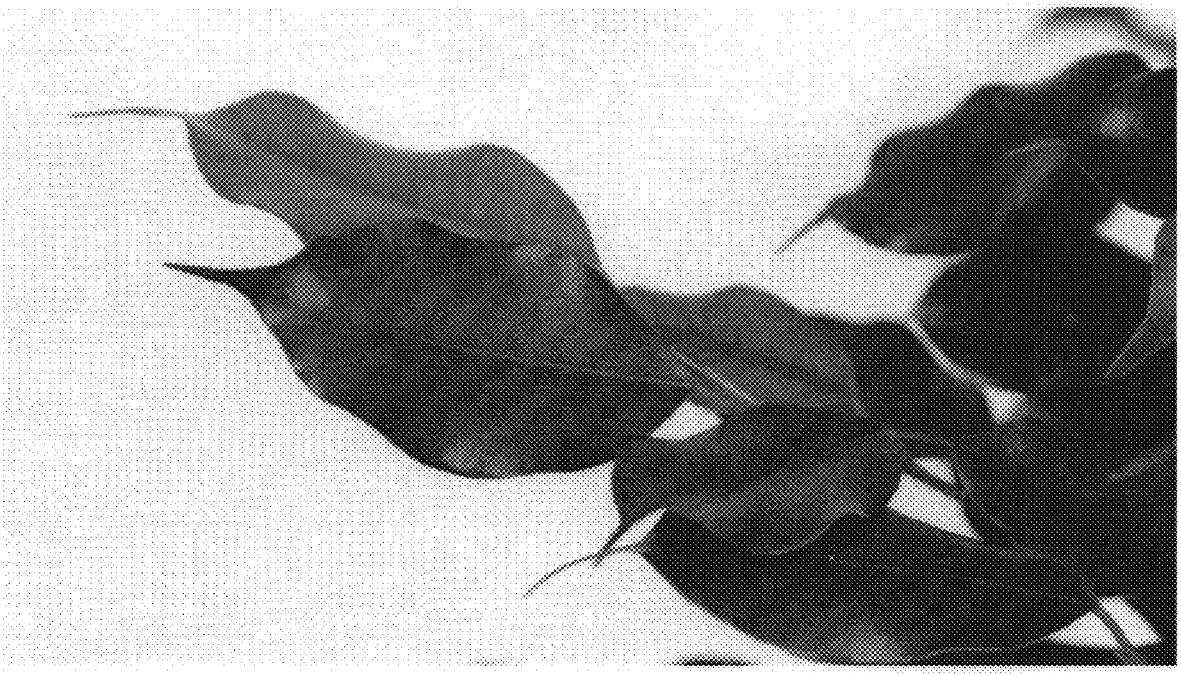
FIG. 2 illustrates, as nearly true as it is reasonably possible to make the same in color photographs of this type, the typical foliage of 'ESFIBE1801'.

The following observations and measurements were made in February of 2019 and describe a sample set of six 26 week-old 'ESFIBE1801' plants grown in 15 cm nursery pots, two plants per container, at a greenhouse in Gravenzande, The Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESFIBE1801' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'ESFIBE1801' and comparisons with the parent plant and most similar commercial variety of *Ficus* are provided below.

Plant description:

*Growth habit*.—Upright to broad, upright broadleaf evergreen.

*Plant form*.—Ovate to broad ovate.

*Average height*.—52.3 cm from the soil level to the top of the foliar plane.

*Plant spread*.—Average of 43.8 cm.

*Growth rate*.—Moderately fast.

*Plant vigor*.—Moderately vigorous to vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 15 weeks to produce a marketable finished plant in a 14 cm pot.

*Disease resistance*.—Neither resistance nor susceptibility to typical *Ficus benjamina* pests and diseases has been observed.

*Environmental tolerances*.—Adapt to, at least, USDA Zones 10 through 13 and temperatures as high as 40 degrees Celsius; moderate to high tolerance to rain; moderate tolerance to wind.

Root system:

*General*.—Moderately dense, moderately branched rooting; roots are slightly fibrous.

*Distribution in the soil profile*.—Moderately deep.

*Diameter of roots*.—1.0 mm on average.

*Texture*.—Smooth; no root hairs.

*Color*.—Greyed-orange, nearest to RHS 164A.

Stem:

*General branching habit*.—Solitary main stem, with lateral branching. Stems produce a milky exudate when damaged.

*Main stem*.—Quantity — 1. Attitude — Upright. Near vertical. Aspect — Rounded. Strength — Strong. Color, immature stems — Yellow-green, nearest to RHS 144A. Color, mature stems — Yellow-green, nearest to a combination of RHS 148A and 148B. Color at internodes — Yellow-green, nearest to a combination of RHS 148A and 148B. Color, oldest wood — Greyed-brown, nearest to RHS 199A. Texture — Densely covered with a fibrous layer, colored greyed-brown, nearest to a mixture of RHS 199C and 199D. Moderately covered with small elliptical lenticels; lenticels are approximately 0.6 mm long and 0.3 mm wide and are colored greyed-brown, nearest to RHS 199D. Luster — Slightly glossy.

*Lateral branches*.—Quantity — 27. Length — 17.5 cm. Diameter — 2.0 cm. Internode length — 2.6 cm. Attitude — Outward; at an approximate angle of 45 degrees to the main stems. Shoot tips are semi-erect to horizontal. Aspect — Rounded. Strength — Strong. Color, immature stems — Yellow-green, nearest to RHS 144A. Color, mature stems — Yellow-green, nearest to a combination of RHS 148A and 148B. Color at internodes — Yellow-green, nearest to a combination of RHS 148A and 148B. Texture — Densely covered with a fibrous layer, colored greyed-brown, nearest to a mixture of RHS 199C and 199D. Moderately covered with small elliptical lenticels; lenticels are approximately 0.6 mm long and 0.3 mm wide and are colored greyed-brown, nearest to RHS 199D. Luster — Slightly glossy.

Foliage:

*Arrangement*.—Alternate.

*Division*.—Simple.

*Quantity*.—7 leaves per lateral branch.

*Attitude*.—Relaxed; at an average angle of 40 degrees to the branch.

*Lamina*.—Shape — Narrowly ovate to oblong; leaf tip is short relative to the total length of the lamina. Aspect — Slightly carinate, relatively flat across much of the foliar plane, slightly revolute at and towards the margin with the distal portion curled downward. Dimensions — 7.0 cm long and 3.1 cm wide. Apex — Aristate to caudate. Base — Acute. Margin — Entire; coarsely undulate. Texture and luster of the adaxial surface — Smooth, glabrous and moderately glossy, with small orbicular glands visible along the margins; glands are approximately 0.2 mm in diameter and are colored yellow-green, nearest to RHS 150C. Texture and luster of the abaxial surface — Smooth, glabrous, and very slightly glossy. Color — Juvenile foliage, adaxial surface — Yellow-green, nearest to RHS 144A. Juvenile foliage, abaxial surface — Yellow-green, nearest to RHS 144A. Mature foliage, adaxial surface — Nearest to in between greyed-green and black, RHS N189A and 203A. Mature foliage, abaxial surface — Green, nearest to RHS NN137B. Venation — Pattern — Pinnate. Color, adaxial surface — Green, nearest to RHS NN137C. Color, abaxial surface — Yellow-green, nearest to RHS 152D.

*Stipule*.—Not present.

*Petiole*.—Length — 1.3 cm. Diameter — 1.5 mm. Strength — Strong. Texture — Smooth; glabrous. Luster — Very slightly glossy. Color, adaxial surface — Yellow-green, nearest to RHS 146B. Color, abaxial surface — Yellow-green, nearest to RHS 146B.

Inflorescence: No flowering has been observed to date.

Comparison with the parent plant: Plants of the new cultivar 'ESFIBE1801' differ from the parent, *Ficus benjamina* 'Danielle' (Community Plant Variety Rights grant number 590), in the following characteristics described in Table 1 below.

TABLE 1

| Characteristic | 'ESFIBE1801' | 'Danielle' |
|---|---|---|
| Growth habit. | More upright than 'Danielle'. | More spreading than 'ESFIBE1801'. |
| General coloration of the mature foliage. | Darker green. | Lighter green. |

Comparison with the closest known comparator: Plants of the new cultivar 'ESFIBE1801' differs from the variety, *Ficus* sp. 'ESFIDE161' (Community Plant Variety Rights application number 2016/3129), in the following characteristics described in Table 2 below.

TABLE 2

| Characteristic | 'ESFIBE1801' | 'ESFIDE161' |
|---|---|---|
| Plant height. | Shorter than 'ESFIDE161'. | Taller than 'ESFIBE1801'. |
| Abundance of foliage. | Less abundant. | More abundant. |
| Foliage shape. | Narrowly ovate to oblong. | Broadly ovate. |
| General coloration of the foliage. | Darker green. | Lighter green. |

That which is claimed is:

1. A new and distinct variety of *Ficus* plant named 'ESFIBE1801', substantially as described and illustrated herein.

* * * * *